United States Patent [19]

Stach

[11] Patent Number: 4,536,210
[45] Date of Patent: Aug. 20, 1985

[54] METHOD OF INCREASING THE RECOVERABLE SUGAR FROM SUGAR BEETS

[75] Inventor: Leonard J. Stach, Riverside, Ill.

[73] Assignee: Velsicol Chemical Corporation, Chicago, Ill.

[21] Appl. No.: 492,521

[22] Filed: May 9, 1983

Related U.S. Application Data

[63] Continuation-in-part of Ser. No. 346,687, Feb. 8, 1982, abandoned.

[51] Int. Cl.³ ............................................. A01N 37/20
[52] U.S. Cl. ...................................... 71/118; 71/115; 71/76
[58] Field of Search .......................... 71/118, 115, 76

[56] References Cited

U.S. PATENT DOCUMENTS

| | | | |
|---|---|---|---|
| 2,577,969 | 12/1951 | Jones | 71/118 |
| 3,557,209 | 1/1971 | Richter et al. | 71/118 |
| 3,826,641 | 7/1974 | Porter | 71/86 |
| 3,932,168 | 1/1976 | Stein et al. | 71/105 |
| 4,126,440 | 11/1978 | Moser et al. | 71/118 |

OTHER PUBLICATIONS

Nickell et al., "Effects of Chemicals, etc.", (1965).
Haw. Sugar Tech., pp. 152–163 (1965).
Richter, "Increasing the Quantity, etc.", (1981).
CA 95, 92363h, (1981).
Ochiai et al., "Acid Amides", (1967).
CA 67, 90549w (1967).
Kasztreiner et al., "Benzohydroxamic Acids", (1973).
CA 80, 82438n (1974).

*Primary Examiner*—Glennon H. Hollrah
*Assistant Examiner*—Andrew Duff Meikle
*Attorney, Agent, or Firm*—Robert J. Schwarz

[57] ABSTRACT

This application discloses a method for increasing the recoverable sugar from sugar beet plants by applying to the sugar beet plants an effective amount of a compound having the structural formula:

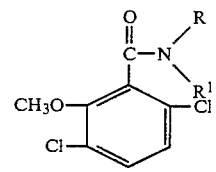

wherein R is selected from the group consisting of hydrogen, alkyl, alkoxy, hydroxy and hydroxyalkyl and $R^1$ is independently selected from the group consisting of alkyl, alkoxy, hydroxy and hydroxyalkyl.

5 Claims, No Drawings

METHOD OF INCREASING THE RECOVERABLE SUGAR FROM SUGAR BEETS

This application is a continuation-in-part of my copending application, Ser. No. 346,687, filed Feb. 8, 1982, now abandoned.

This invention relates to a method of increasing the yield of sugar from sugar beets. More particularly, this invention relates to a method of increasing the recoverable sugar in sugar beets by treating the sugar beet plants during their growth period with benzamides of 2-methoxy-3,6-dichlorobenzoic acid.

The performance of this process requires the use of an effective amount of the benzamide at least two weeks before harvest. The benzamides of dicamba useful in the present method have the following structural formula:

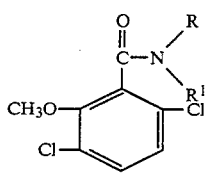

wherein R is selected from the group consisting of hydrogen, alkyl, alkoxy, hydroxy and hydroxyalkyl and $R^1$ is independently selected from the group consisting of alkyl, alkoxy, hydroxy and hydroxyalkyl.

It is most preferred that the alkyl substituants have a maximum of six carbon atoms.

The above described compounds can be prepared by reacting the corresponding acid chloride with the necessary amine as follows:

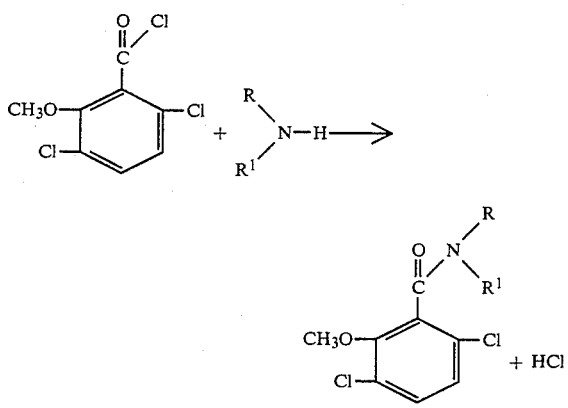

wherein R and $R^1$ are as previously defined.

The following examples demonstrate the preparation of the compounds useful in performing the disclosed process. These benzamide compounds are described in the literature.

EXAMPLE 1

Preparation of N,N-dimethyl-2-methoxy-3,6-dichlorobenzamide

Water (150 ml) and potassium carbonate (300 grams) were placed in a 3-liter, 3-necked glass reaction flask equipped with stirrer, thermometer and an ice-water bath. After the exotherm subsided, ether (70 ml) was added to the mixture in small portions with stirring for ten (10) minutes. 2-methoxy-3,6-dichlorobenzoylchloride (300 grams; 1.25 mole) was added dropwise with stirring at a rate such that the reaction temperature did not rise above 7° C. The reaction mixture was stirred overnight. The salts were filtered off and the filtrate washed with soda ash (20%). The ether was dried over magnesium sulfate, filtered and distilled on a steam bath. The liquid residue was distilled through a Claisen head in vacuo. The desired product was collected at 107°–108° C. 0.17 mm Hg. pressure and was water white.

EXAMPLE 2

Preparation of N,N-bis(2-hydroxyethyl)-2-methoxy-3,6-dichlorobenzamide

Diethanolamine (11 grams; 0.105 mol), triethylamine (12 grams) and toluene (100 ml) were placed in a 250 ml, 3-necked glass reaction flask equipped with stirrer, thermometer and reflux condenser. 2-methoxy-3,6-dichlorobenzoic acid chloride (23.9 grams; 0.1 mol) in toluene (25 ml) were added to the reaction mixture by means of an addition funnel. The reaction mixture was stirred for two hours and then filtered. The recovered solid material was heated in ethyl acetate and filtered. Toluene was added to the oily residue, heated to dissolve the oil and cooled. The desired product first formed as an oil and then crystalized. The product weighed 23.6 grams representing a yield of 76%.

EXAMPLE 3

Preparation of N-hydroxy-2-methoxy-3,6-dichlorobenzamide

Potassium carbonate (359.7 grams; 2.6 moles) was dissolved in water (400 ml) in a 5-liter, 3-necked glass reaction flask equipped with stirrer, thermometer and addition funnel. Ether (2.5 liters) was added to the contents of the flask which were cooled to 0°–5° C. by use of an ice-water, salt bath. Hydroxylamine hydrochloride (181.7 grams; 2.6 moles) was added portionwise to the cooled, stirred solution. The solution was stirred for an additional hour after completion of the addition. 2-methoxy 3,6-dichlorobenzoic acid chloride (479.7 grams; 2.0 moles) was added dropwise from the addition funnel while maintaining the temperature of the mixture at 0°–5° C. The mixture was stirred for an additional two hours after completion of the addition. The white solid separated out. It was broken up by vigorous stirring and filtered. Dilute hydrochloric acid (10%) was prepared from concentrated hydrochloric acid solution (369 grams) and water (1030 mls). The solid was added to the dilute hydrochloric acid and stirred for two hours. Water was added to the Buchner filter containing the solution and filtered by the use of suction. The filter cake was washed with water and dried under vacuum. The product weighed 433 grams, representing a yield of 92%.

EXAMPLE 4

Preparation of N-Methyl-2-Methoxy-3,6-Dichlorobenzamide

Methylamine (146.1 grams; 4.70 moles) contained in 40% aqueous methyl amine solution (365.4 grams) was placed in a 3-liter, 3-necked glass reaction flask equipped with addition funnel, stirrer, thermometer and reflux condenser and containing ether (1200 ml) cooled to 4° C. 2-methoxy-3,6-dichlorobenzoic acid chloride (375 grams; 1.56 moles) in ether (50 ml) was added dropwise with stirring maintaining the temperature below 8° C. After the completion of the addition the reaction mixture was stirred for an additional two hours at a temperature of between 2° and 5° C. The insoluble white solid was filtered with suction, washed with water, transferred to a 3-liter beaker and stirred fifteen (15) minutes with 10% sodium carbonate (2 liters). The insoluble white solid was filtered with suction, washed with water and dried. The product weighed 352 grams and had a melting point of 172.5°–175° C.

To effect the method of this invention, sugar beet plants are treated at a comparatively late stage of development with an effective amount of an active compound described above. This treatment is carried out during that stage of development of the sugar beet plant wherein sugar formation takes place. Thus, under normal growing conditions and common cultivation practice the active compounds described can be applied to the sugar beet plants during the period of from about 2 to about 10 weeks before harvesting and preferably during the priod of from about 4 to 7 weeks before harvesting. The use of nitrogen fertilizer, when employed during the cultivation of the sugar beets, is advantageously discounted before the application of the active compounds of this invention.

The amount of the active compound of this invention required to effectively increase the recoverable sugar from sugar beets can vary somewhat depending on such factors as the time of application, the weather, crop density, and the like. Generally, an amount of at least about 0.1 ounces per acre and preferably an amount of from about 0.5 ounces per about 20 ounces per acre can be used. While amounts greater than those mentioned can be used, they will not result in an advantage that would warrant their expense and are, therefore, not practical.

For practical use in treating sugar beets, the compounds of this invention are generally incorporated into compositions or formulations which comprise an inert carrier and an effective amount of such a compound. These compositions enable the active compounds to be conveniently applied to the sugar beets in any desired quantity. These formulations can be liquids such as solutions, aerosols or emulsifiable concentrates or they can be solids such as dusts, granules or wettable powders.

The preferred compositions are liquid formulations, particularly emulsifiable concentrates. Emulsifiable concentrates comprise an active compound, according to this invention, and as the inert carrier, a solvent and an emulsifier. Such emulsifiable concentration of active compound for application as sprays to the sugar beets. The emulsifiers most commonly used in these concentrates are nonionic or mixtures of nonionic with anionic surface-active agents. With the use of some emulsifier systems an inverted emulsion (water-in-oil) can be prepared.

Solid formulations such as dusts, for example, can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

Typical formulations according to the present invention useful for increasing the recoverable sugar in sugar beets are illustrated in the following examples wherein the quantities are in parts by weight.

EXAMPLE 5

Preparation of an Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

| | |
|---|---|
| N—methyl-2-methoxy-3,6-dichlorobenzamide | 25 |
| Sodium lauryl sulfate | 2 |
| Sodium lignin sulfate | 3 |
| Kerosene | 70 |

EXAMPLE 6

Preparation of a Wettable Powder

The following components are mixed intimately in conventional mixing or blending equipment and are then ground to a powder having an average particle size of less than about 50 microns. The finished powder is dispersed in water to give the desired concentration of active compound.

| | |
|---|---|
| N,N—dimethyl-2-methoxy-3,6-dichlorobenzamide | 50 |
| Fuller's earth | 47 |
| Sodium lauryl sulfate | 2.5 |
| Methyl cellulose | 0.5 |

EXAMPLE 7

Preparation of a Dust

The following ingredients are mixed thoroughly and are then ground to an average particle size of less than about 50 microns to give a dust suitable for application with conventional dusting equipment.

| | |
|---|---|
| N—hydroxy-2-methoxy-3,6-dichlorobenzamide | 10 |
| Powdered talc | 90 |

The increase in the recoverable sugar from sugar beet plants by the application of the disclosed compounds was demonstrated by tests performed using a standard procedure. Sugar beet plants were sprayed with an approximately diluted emulsifiable concentrate of the test compound. The plants were surface irrigated at two week intervals to maintain normal growth. The crop was harvested and the recoverable sugar determined and measured on a percent basis in comparison to controls. The results of these tests are reported in Tables 1–4. Tables 5, 5A and 5B contain the results of a record test using the same procedures, but using four different times of applying the compound of Example 1.

TABLE 1
PRODUCT OF EXAMPLE 1

| RATE OF APPLICATION (Ounces/Acre) | BEET RECOVERY (Tons/Acre) | Percent Of Check | SUGAR RECOVERY (Lbs/Acre) | Percent Of Check |
|---|---|---|---|---|
| 2 | 20.4 | 103.0 | 3991 | 101.4 |
| 8 | 21.8 | 110.1 | 4081 | 103.7 |
| 20 | 26.3 | 132.8 | 5176 | 131.5 |
| Check | 19.8 | — | 3932 | — |

TABLE 2
PRODUCT OF EXAMPLE 2

| RATE OF APPLICATION (Ounces/Acre) | BEET RECOVERY (Tons/Acre) | Percent Of Check | SUGAR RECOVERY (Lbs/Acre) | Percent Of Check |
|---|---|---|---|---|
| 2 | 19.3 | 102.1 | 3805.2 | 103.3 |
| 8 | 21.6 | 114.3 | 4178.0 | 113.5 |
| 20 | 22.2 | 117.5 | 4478.3 | 121.6 |
| Check | 18.9 | — | 3681.7 | — |

TABLE 3
PRODUCT OF EXAMPLE 3

| RATE OF APPLICATION (Ounces/Acre) | BEET RECOVERY (Tons/Acre) | Percent Of Check | SUGAR RECOVERY (Lbs/Acre) | Percent Of Check |
|---|---|---|---|---|
| 1 | 21.4 | 106.5 | 5188 | 106.9 |
| 2 | 18.9 | 94.0 | 4588 | 94.5 |
| 4 | 25.5 | 126.9 | 6492 | 133.7 |
| 8 | 17.3 | 86.1 | 4394 | 90.5 |
| 16 | 17.9 | 89.1 | 4746 | 97.8 |
| Check | 20.1 | — | 4855 | — |

TABLE 4
PRODUCT OF EXAMPLE 4

| RATE OF APPLICATION (Ounces/Acre) | BEET RECOVERY (Tons/Acre) | Percent Of Check | SUGAR RECOVERY (Lbs/Acre) | Percent Of Check |
|---|---|---|---|---|
| 1 | 22.0 | 106.2 | 5334 | 99.5 |
| 2 | 23.2 | 112.0 | 5920 | 115.0 |
| 4 | 20.5 | 99.0 | 5251 | 98.2 |
| 8 | 20.3 | 98.0 | 5376 | 100.4 |
| 16 | 24.7 | 119.3 | 6372 | 119.3 |
| Check | 20.7 | — | 5357 | — |

TABLE 5
PRODUCT OF EXAMPLE 1
TIME OF APPLICATION

| RATE OF APPLICATION OUNCES/ACRE | AT PLANTING Pounds Of Beets | 80% OF ROW CLOSURE Pounds Of Beets | 6 WEEKS BEFORE HARVEST Pounds Of Beets | 3 WEEKS BEFORE HARVEST Pounds Of Beets |
|---|---|---|---|---|
| 4 | 185.4 | 182.8 | 183.5 | 177.8 |
| 8 | 170.2 | 168.3 | 174.1 | 170.8 |
| 16 | 168.0 | 167.4 | 183.3 | 172.5 |
| 32 | 171.8 | 178.9 | 166.9 | 166.6 |
| Check | 166.8 | 179.6 | 162.3 | 167.5 |

TABLE 5A
PRODUCT OF EXAMPLE 1
TIME OF APPLICATION

| RATE OF APPLICATION OUNCES/ACRE | AT PLANTING Recoverable Sugar (Pound/Acre) | 80% OF ROW CLOSURE Recoverable Sugar (Pound/Acre) | 6 WEEKS BEFORE HARVEST Recoverable Sugar (Pound/Acre) | 3 WEEKS BEFORE HARVEST Recoverable Sugar (Pound/Acre) |
|---|---|---|---|---|
| 4 | 8859.4 | 8856.1 | 9024.6 | 8531.7 |
| 8 | 8211.0 | 8127.9 | 8244.9 | 8583.7 |
| 16 | 7989.2 | 7948.9 | 8514.0 | 8389.1 |
| 32 | 7994.6 | 8779.5 | 8018.6 | 8324.0 |
| Check | 7858.8 | 8798.1 | 7509.0 | 7848.5 |

TABLE 5B
PRODUCT OF EXAMPLE 1
TIME OF APPLICATION

| RATE OF APPLICATION OUNCES/ACRE | AT PLANTING Percent Sugar | 80% OF ROW CLOSURE Percent Sugar | 6 WEEKS BEFORE HARVEST Percent Sugar | 3 WEEKS BEFORE HARVEST Percent Sugar |
|---|---|---|---|---|
| 4 | 16.9 | 16.9 | 17.1 | 16.9 |
| 8 | 16.8 | 17.0 | 16.8 | 17.6 |
| 16 | 16.5 | 16.8 | 16.6 | 17.1 |
| 32 | 16.4 | 17.2 | 16.9 | 17.4 |
| Check | 16.5 | 17.2 | 16.2 | 16.7 |

I claim:
1. A method for increasing the recoverable sugar from sugar beets which comprises contacting the sugar beet plants during the period of from about two to about ten weeks before harvest with an effective amount of a sugar ripener having the following structural formula:

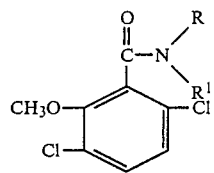

wherein R is selected from the group consisting of hydrogen and lower alkyl and R¹ is lower alkyl.

2. The method of claim 1 wherein the sugar beet plants are contacted with at least 0.5 ounces per acre of the sugar ripener during the period of from about two to about ten weeks before harvest.

3. The method of claim 1 wherein the sugar ripener is N,N-dimethyl-2-methoxy-3,6-dichlorobenzamide.

4. The method of claim 1 wherein the sugar ripener is N-methyl-2-methoxy-3,6-dichlorobenzamide.

5. The method of claim 1 wherein the sugar ripener is contacted with the sugar beets from about four to about seven weeks before harvest.

* * * * *